United States Patent [19]
Khalil

[11] Patent Number: 5,056,526
[45] Date of Patent: Oct. 15, 1991

[54] DEVICE FOR GLOBAL EVALUATION OF THE LEFT VENTRICULAR EJECTION FRACTION BY THERMODILUTION

[76] Inventor: Hassan H. Khalil, P.O. Box 296, Alexandria, Egypt

[21] Appl. No.: 428,160

[22] Filed: Oct. 27, 1989

[51] Int. Cl.$^5$ ............................................... A61B 5/02
[52] U.S. Cl. .................................. 128/692; 128/786; 128/713
[58] Field of Search ............... 128/692, 697, 784, 786, 128/736, 27, 31, 713

[56] References Cited

U.S. PATENT DOCUMENTS

| | | | |
|---|---|---|---|
| 3,075,515 | 1/1963 | Richards | 128/692 |
| 4,153,048 | 5/1979 | Magrini | 128/692 |
| 4,576,182 | 3/1986 | Norman | 128/736 |
| 4,856,530 | 8/1989 | Vandervelden | 128/692 |

*Primary Examiner*—Francis Jaworski
*Assistant Examiner*—George Manuel
*Attorney, Agent, or Firm*—Thomas R. Vigil

[57] ABSTRACT

The left ventricular catheter is adapted to be inserted into the heart and has an upstream heater winding near the distal catheter tip. Pulses of regulated electrical energy triggered by the R-wave of an electrocardiogram are supplied to the heater winding on the catheter so that successive heat energy is generated and dissipated in the blood volume of the left ventricle during successive diastoles. A resistance thermometer is mounted downstream from the heater winding to measure successive temperature increases as the heart beats over a 5-10 second measuring period, whereby a exponential temperature rise is recorded. To cancel deviation of temperature readings caused by heat dissipation from the lead wire conductors bypassing the thermometer to the catheter heater, lead wire conductors are provided to an external dummy load heater winding for bypassing the thermometer. By alternating high frequency electrical energy from the catheter heater winding during diastoles to the dummy load heater winding during systoles through the lead wire conductors, a constant environmental temperature is maintained for the thermometer to measure temperature rise after thermodilution for evaluation of the global ejection fraction during diagnostic and intervention catheterization.

7 Claims, 8 Drawing Sheets

DEVICE FOR GLOBAL EVALUATION OF THE LEFT VENTRICULAR EJECTION FRACTION BY THERMODILUTION

BACKGROUND OF THE INVENTION

1. Field of the Invention

The present invention relates to a new left ventricular thermodilution catheter devised to evaluate the global ejection fraction during diagnostic and interventional catheterization.

2. Description of the related art including information disclosed under 37 CFR §§1.97-1.99

Attempts to measure cardiac output started late last century with Stewart's first determination of this value using continuous injection of hypertonic saline as an indicator and obtaining an auditory signal During the following decades, several other continuous and single injection indicator dilution techniques to measure cardiac output of the right and left ventricles both at rest and during exercise were developed and widely applied. These methods have the minute volume of cardiac output as their common objective. They do not proceed to realize the more specific value of ventricular function, namely, ventricular ejection fraction, particularly that of the left ventricle, which is the ratio of the stroke volume of the left ventricle over end-diastolic volume of the left ventricle. The left ventricular ejection fraction is the global index of fiber shortening and is now considered to be one of the most sensitive values of left ventricular function.

Accurate determination of the global ejection fraction of the left ventricle has become a practical step to obtain an over all function of the left ventricle. Further measures to obtain segmental and regional values may not always be required. Present diagnostic values used to determine the left ventricular ejection fraction include, two dimensional echocardiography, digital angiography, contrast ventriculography and radionuclide ventriculography. More recently, ultra fast computed tomography and nuclear magnetic resonance were adapted to measure these values. With the exception of two dimensional echocardiography, all other sophisticated systems are only available in specialized centers.

Ejection fraction measures by two dimensional echocardiography carry with them a significant percentage of error. This appears while measuring the basal portion of the ventricle with a gradually more acutely directed angle relative to the long axis of the ventricle. The progressively more oblique angles underestimate the normal apex to base segmental variability.

SUMMARY OF THE INVENTION

According to the present invention a method for multiple accurate determinations of the global left ventricular ejection fraction by means of a newly devised left ventricular catheter is proposed Based on thermodilution, this method is exactly similar to that of continuous dye dilution and is based on the same principles except that here the body acts as a high capacity heat sink, so that recirculation of previously heated blood is both delayed and minimized.

The catheter disclosed herein is a left ventricular pigtail catheter with an upstream heating coil over a distal segment adapted to be introduced into the cavity of the left ventricle, while a resistance thermometer (bifilar platinum resistance or thermistor) is placed downstream over a segment of the catheter placed in the ascending aortic valve. A separate second heater coil, forming a dummy load of identical resistance to the resistance of the upstream heating coil, is situated external to a patient receiving the catheter and is periodically connected by a switch to the resistance thermometer when the upstream heating coil is periodically disconnected from the thermometer, so that high frequency current can be continuously supplied to the resistance thermometer to maintain the thermometer at a constant temperature even when the upstream heating coil is deenergized.

The catheter is preferably a thin walled, braided DACRON TM catheter. The present invention is a new device for multiple evaluation of the global left ventricular ejection fraction by thermodilution using a newly designed left ventricular catheter system. An upstream high frequency electrical energy heater winding mounted on the distal segment of the catheter to be placed in the cavity of the left ventricle dissipates during successive diastoles ECG triggered heat pulses at a predetermined constant rate, to blood volume in the left ventricle over a 5-10 second measuring period. During successive systoles, the high frequency electrical energy is diverted to an external dummy load winding of identical impedance to that of the upstream catheter heater winding through an electronic switch. A downstream platinum resistance thermometer or thermistor in the ascending aorta measures the successive stepwise temperature increases with systolic ejections. An exponential pattern of temperature rise not exceeding 0.05° in steps following each heart beat is recorded. The global ejection fraction is the ratio of successive increases in temperature while the heart beats for the 5-10 second measuring period.

The capacity for this new left ventricular catheter system for evaluation of the global ejection fraction renders it a valuable device during diagnostic and interventional catheterization.

DESCRIPTION OF THE PREFERRED EMBODIMENTS

Figures 1, 2, 3:
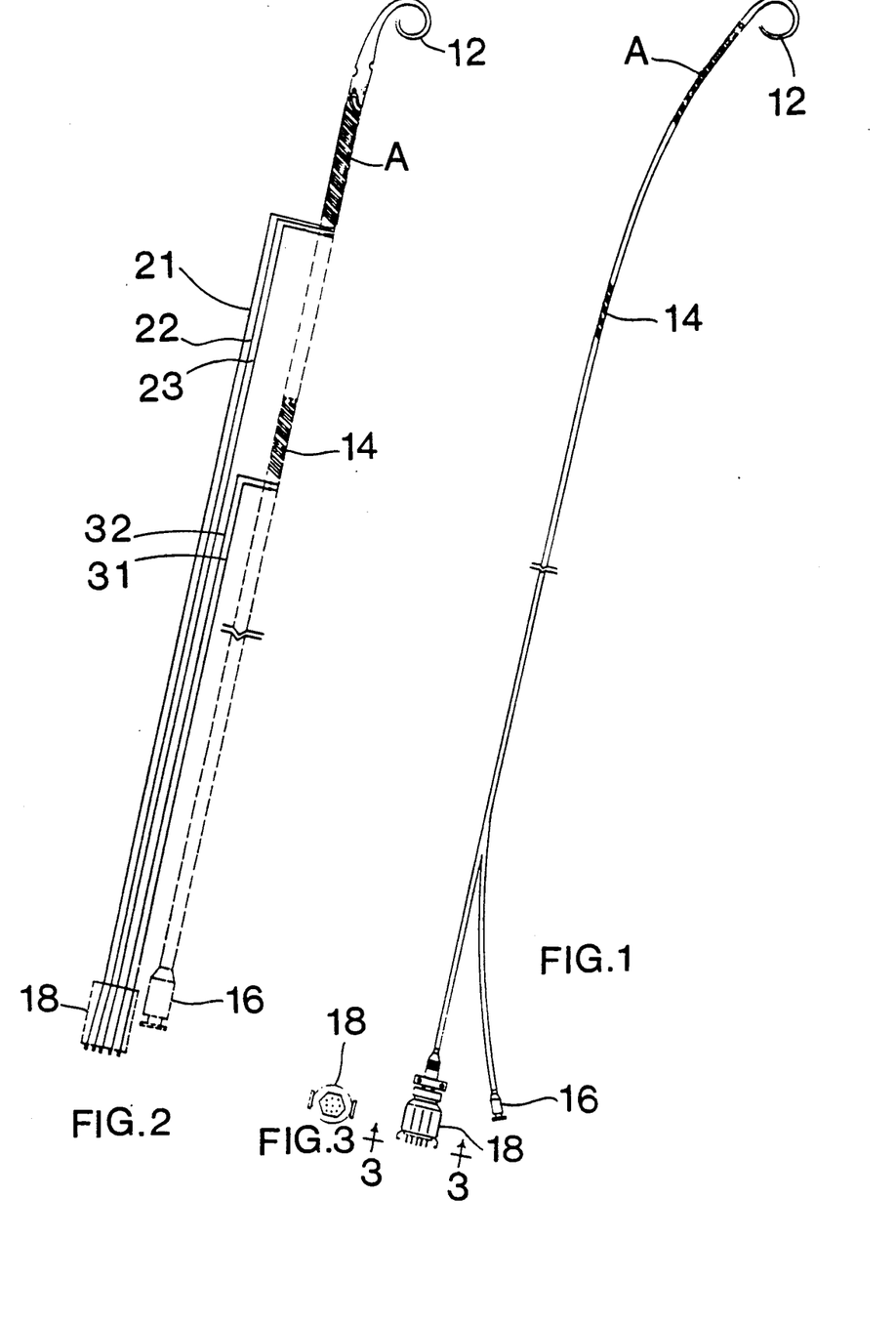
FIG. 1 is a plan view of one embodiment of the catheter of the present invention.
FIG. 2 is an expanded plan view of the electrical wire conductor connections to a heater coil and to a resistance thermometer on the catheter show in FIG. 1.
FIG. 3 is an end view of a pug at the proximal end of the catheter shown in FIG. 1 and is taken along line 3—3 of FIG. 1.

As shown in FIG. 1, one embodiment of a left ventricular pigtail catheter 10 of the present invention has a pigtail distal tip 12, a heating coil or heater winding A just proximal of the tip 12, a platinum resistance thermometer 14 proximal of the heating coil A, and a Luer Lock 16 and an electrical plug 18 at a proximal end of the catheter 10.

As shown in FIG. 2, three wire conductors or lead wires 21, 22 and 23 extend in the catheter 10 from the heater coil A to the plug 18 and two wire conductors or lead wires 31, 32 and 33 extend from the resistance thermometer 14 to the plug 18.

The heating coil A comprises one or two constantan wire connected in parallel, tightly wound in a bifilar fashion around a distal segment of the left ventricular pigtail catheter 10 to give a total resistance with its lead wires 21-23 of 50 ohms.

Since the size of wire conductors used determines the length and surface area of the coil A, two wires in parallel which were 0.09 mm outside diameter wire were found suitable to give a heater coil A 4 cms long on a 7 F catheter, and two wires in parallel of 0.1 mm outside diameter were suitable for a heater coil A 5 cms long on a 7.4 F catheter.

The number of wires in parallel and the diameter of each wire as well as the size of the outside tubular catheter 10 over which the coil A is wound may be decreased to a single wire on a smaller sized catheter according to the size of the heart to be investigated. For example, a single bifilar winding of 0.1 mm outside diameter of constantan wire gives a heater coil A 2 cms long on a 5 F catheter suitable for pediatric use.

A single bifilar winding with a heavier wire of 0.14 mm outside diameter may be used to give a heating coil A around 4 cms on a 7.4 F catheter, but then the surface of the heater coil A would be uneven and require more polyurethane coating to smooth its surface. In addition, it would need a longer time for the heat to dissipate.

The lead wires are preferably thin copper wires having 0.13 mm outside diameter which connect the two proximal ends of the heater coil A to the plug 18 and are tightly wound over the catheter 10. During the application of electrical energy, these wires offer a certain amount of resistance of the passing current and hence a minute fraction of the total heat introduced dissipates from these lead wires before reaching the heater coil.

In one preferred embodiment of the catheter 10 of the present invention, this fraction is about 4% (48 ohms heater coil A and 2 ohms lead wires) of the total heat introduced and is considered as heat loss before reaching the left ventricle.

A certain length of the lead wires passes under the coils of the resistance platinum thermometer 14. Therefore part of the heat dissipating from the segment underlying the resistance or adjacent to a thermistor 34 (which in the catheter 10 shown in FIGS. 4 and 5 replaces the resistance thermometer 14 in the catheter 10 shown in FIGS. 1 and 2) is directly conducted through the catheter wall to either of these temperature measuring transducers or sensors before thermodilution.

This direct conduction from the wires to the thermometer 14 or thermistor 34 creates a significant error during the measurements since it induces an unknown fraction of the temperature to rise. To solve this basic technical problem, an electrical heating circuit 40 as shown in FIGS. 10 and 11 is constructed in the manner described below in accordance with the teachings of the present invention.

Figures 4, 5:
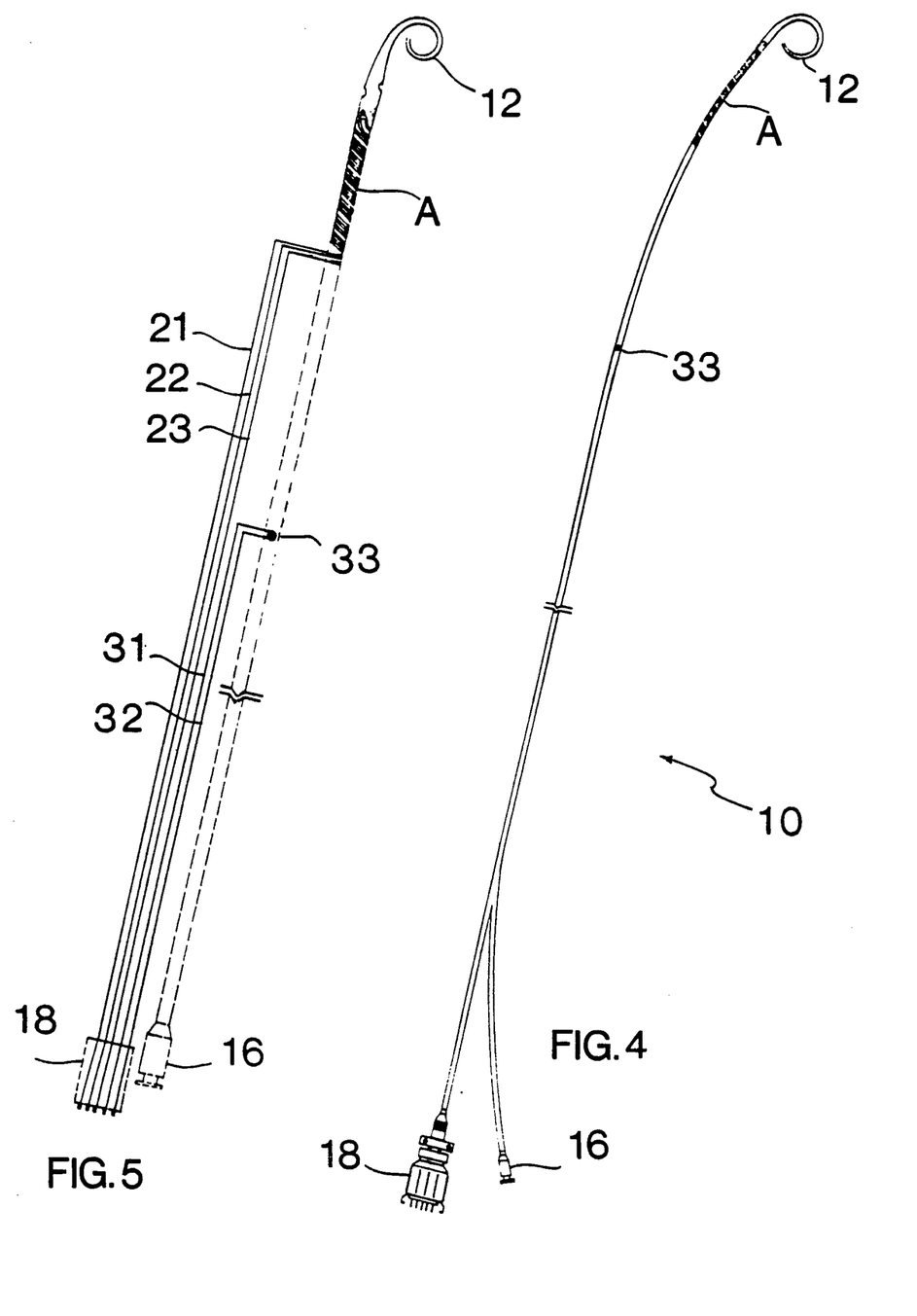
FIG. 4 is a plan view of another embodiment of the catheter of the present invention.
FIG. 5 is an expanded plan view of the electrical wire conductor connections to a heater coil or heating winding and to a thermistor on the catheter show in FIG. 4.
Figure 10:
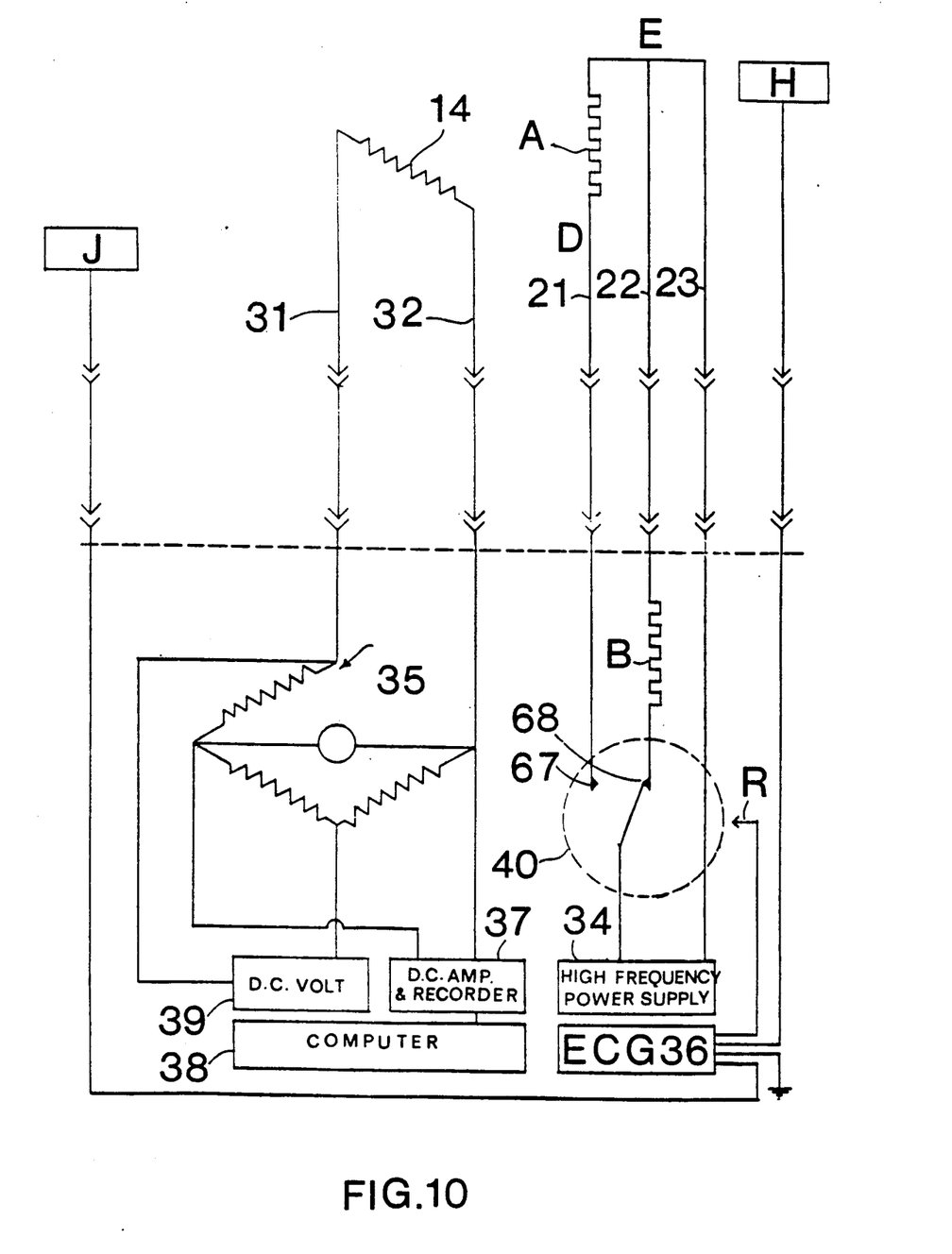
FIG. 10 is an schematic electrical circuit diagram of the measuring circuit of the catheter shown in FIG. 1 or in FIG. 4.
Figure 11:
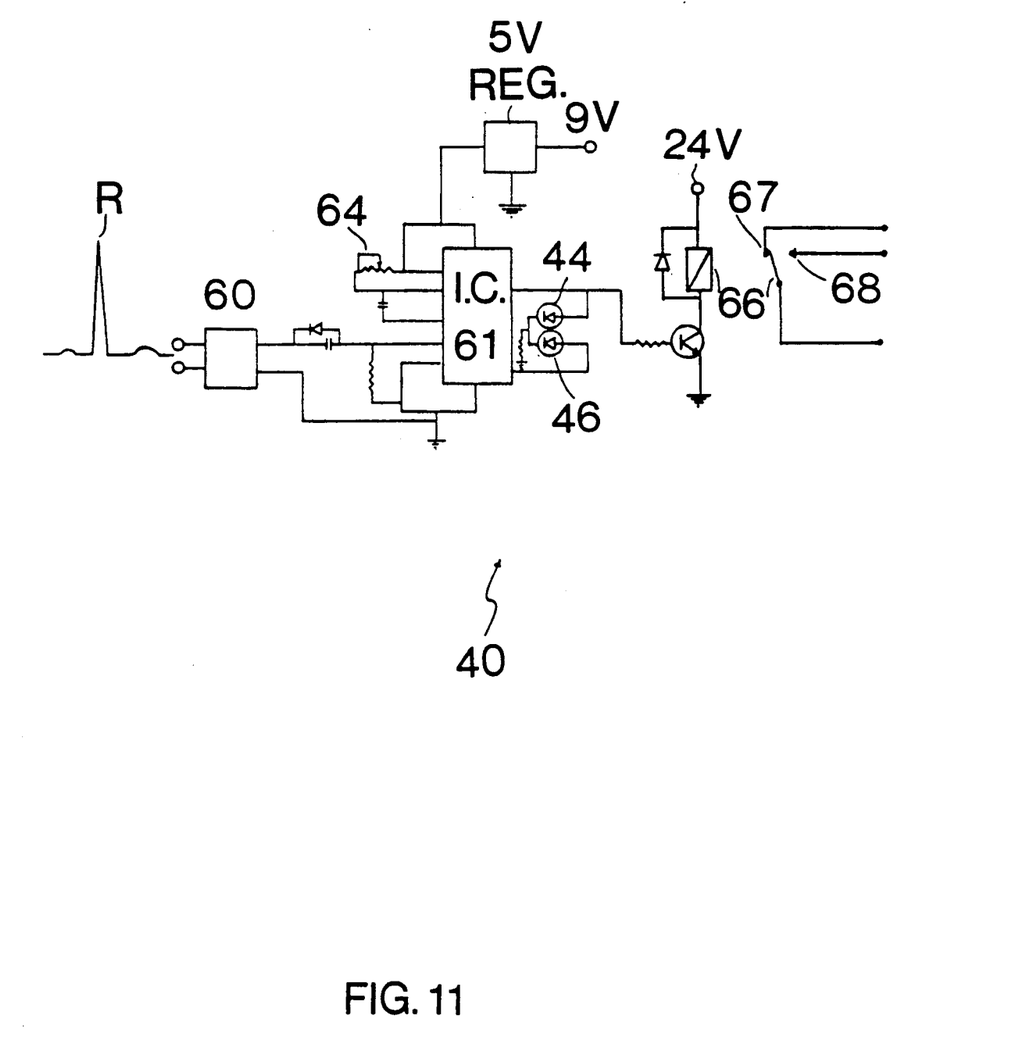
FIG. 11 is a more detailed electrical circuit diagram of a D.C. amplifier and electronic switch which are shown in FIG. 10 and which are activated by an R wave electrocardiogram.

As shown in FIGS. 10 and 11, a second heater coil B forming a load of identical resistance of 50 ohms is prepared and placed inside an external cabinet (external of the patient receiving the catheter 10) with a built-in electronic switch 42 with two light emitting diodes 44 and 46 (FIG. 5).

The three lead wires 21-23 are soldered to the ends of a bifilar wound heater coil A, one lead wire at end D (FIG. 10) and two lead wires at end E (FIG. 10). These connections of lead wires direct high frequency current from the circuit 40 to reach the dummy load heater coil B via the two lead wires connected together at the end E on the catheter 10.

On switching high frequency current from the catheter heater coil A to the dummy load, heater coil B, no change in temperature is registered by the downstream temperature measuring transducer, whether it is a platinum resistance thermometer 14 or thermistor 34 since this element is kept at a constant environmental temperature by equally heating it to a very slight degree throughout the measuring time or period.

The platinum resistance thermometer 14 is reserved for standard catheters used in clinical research studies in man and experimental animals comprises a platinum resistance winding in the form of polyurethane coated platinum wire of 0.03 mm outside diameter in a bifilar winding over 1-3 cms along the tubular catheter according to the size of the heart to be investigated, to be placed in the ascending aorta 6-8 cms distal to the aortic valve with a mean distance of approximately 10 cms between its midpoint and the heater winding.

Before winding the platinum wire, a thin layer of coating with flexible epoxy, Araldite GY 250 and Hardener HY 2963 "CIBA" 0.02 mm diluted in acetone, is first applied on the 1-3 segment of the catheter designed for the platinum bifilar winding to strengthen the walls of this segment. This step is carried out in order to minimize the strain effects on the wound platinum induced by the changing systolic and diastolic pressures on its linear temperature coefficient of resistivity.

In the alternative a thermistor 33 can be used in place of the resistance thermometer 14 used in the catheter 10 shown in FIGS. 1 and 2. Thermistors have the advantage of easy mounting onto the surface of the catheter 10, they are relatively inexpensive and are therefore suitable for single use disposable catheters for use in clinical studies, cardiac catheterization, before and after cardiac surgery and whenever measures of the global ejection fraction are indicated.

A thermistor 34 suitable for blood flow measures is mounted on the surface of the segment of the catheter designed to lie in the ascending aorta 6-8 cms from the aortic valve (FIGS. 4 and 5).

A layer of woven or braided fine Dacron 0.02 mm in diameter separates the platinum resistance thermometer or thermistor from the underlying lead wires 21-23 to heater coil A.

The lead wires 31 and 32 of the platinum resistance thermometer 14 or thermistor 33 comprise two copper wires tightly wound at a wide angle over the catheter and soldered separately to the proximal ends of the platinum wires or thermistor wires to connect them to the plug 18.

Platinum has a linear temperature coefficient of resistivity ($a = 0.0039$) between 0 and 100° C., and is accepted as the element for standard thermometry. When wound as described along approximately 1-3 cms of the catheter shaft, it gives the mean temperature of the blood flowing in the ascending aorta and the mean temperature rise with each heart beat when heat is applied. However, other less expensive elements or alloys with high temperature coefficient of resistivity could be used instead, such as nickel (0.006).

The distal and proximal ends of heater coil (A) and resistance thermometer are anchored to the catheter by a fine Dacron winding. These are then coated by a layer of flexible epoxy for 2-3 mm to further insulate these points and increase their durability. Finally, the catheter 10 and its wound wires are coated with two thin layers of polyurethane diluted 50% in ethyl acetate and cured at 120° C. for 30 minutes. The terminal hole and the two side holes are left patent for pressure measurements and possibly for angiographic studies.

The catheters 10 shown in FIGS. 1-5 were constructed from thin walled braided DACRON ™.

Other heat resistant extruded flexible catheters with or without a nylon core may be used instead. Extruded flexible polyurethane or teflon catheters or other plastic materials are also suitable as long as there is a wide temperature range between the temperature rise of the catheter wall from the rate of heating introduced for 5 seconds with the catheter 10 in still air and the heat tolerance of the catheter material Temperature rise in still water is less than 10% of that in still air and would not possibly induce any damage to the rapidly moving endocardium during the interrupted short intervals of heating 5-10 seconds measuring time.

Figure 6A:
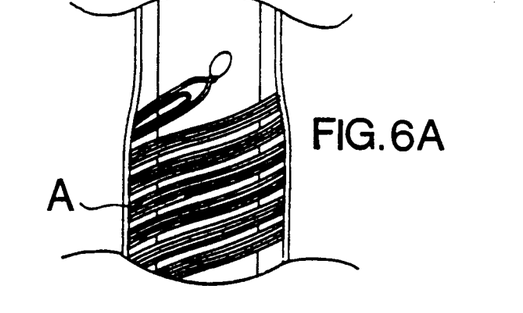
FIGS. 6A, 6B and 6C are fragmentary views with portions broken away of sections of the catheter shown in FIG. 1 containing the heater coil or heater winding.
Figure 6B:
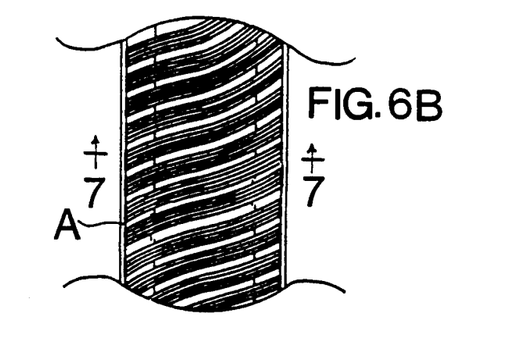
Figure 6C:
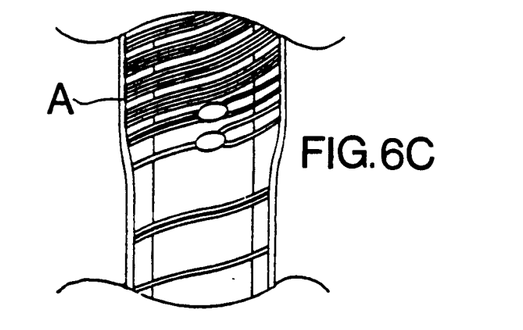
Figure 7:
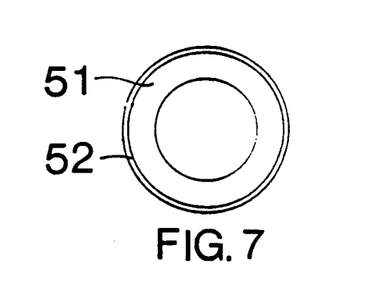
FIG. 7 is a sectional view of the catheter in the area of the heater coil and is taken along line 7—7 of FIG. 6B.

FIGS. 6A-7 show the above described construction of the heater coil A on the catheter 10. In FIG. 7, the catheter wall 51 is shown coated with a polyurethane coating 52.

Figure 8:
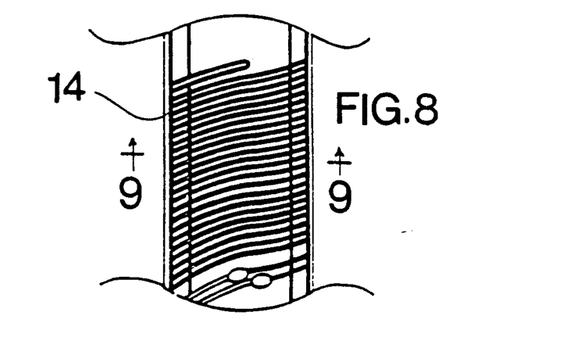
FIG. 8 is a fragmentary view of with portions broken away of a section of the catheter shown in FIG. 1 containing the resistance thermometer.
Figure 9:
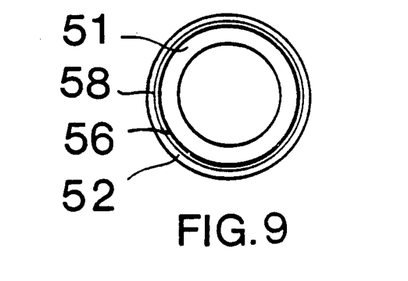
FIG. 9 is a sectional view of the catheter in the area of the resistance thermometer and is taken along line 9—9 of FIG. 8.

FIGS. 8 and 9 show the above described construction of the resistance thermometer 14. In FIG. 9 the catheter inner wall 51 is shown having a thin epoxy layer 56 and a woven or braided DACRON ™ layer 58 is shown beneath the polyurethane coating 52

Exposure of the heater coil A on the catheter 10 to 100 KHz high frequency current causes successive heat pulses to be applied during diastole and triggered by the R wave of an electrocardiogram. This supplying of electrical current is carried out by the electronic switch 42 (FIGS. 10 and 11) activated by the R wave of the electrocardiogram. On receiving the voltage of the R wave through a D.C. amplifier 60, the electronic switch 42 diverts the high frequency current to the dummy load heater coil B during the systoles and directs it to the heater coil A on the catheter 10 during the diastoles of the cardiac cycles occurring during the 5-10 seconds of the measuring time through power transistors 61 and 63. As is known in the art, if desired, and as is well known in the electrical art, a relay switch can be used instead of the power transistor 61, 63.

Figure 12:
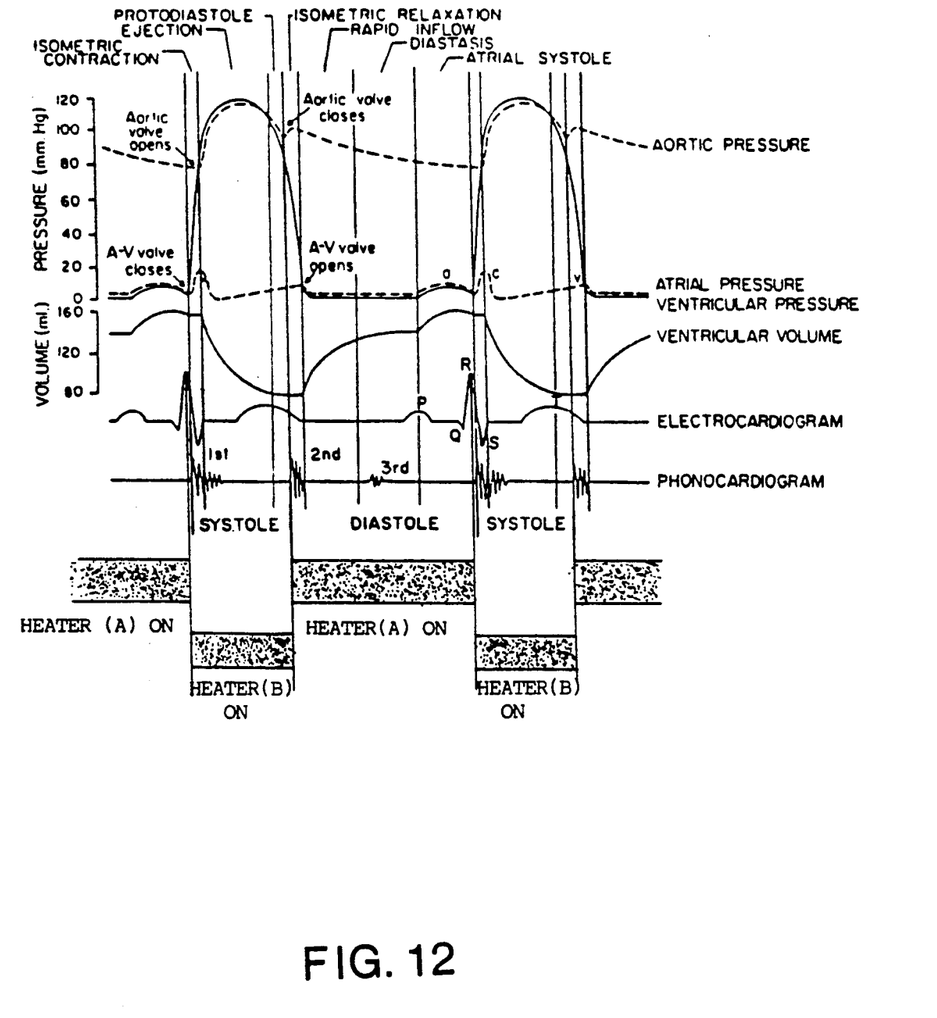
FIG. 12 is a graph of heart pressure and volume over time and shows activation of the electronic switch shown in FIG. 11 by the R wave of an electrocardiogram.
Figure 13:
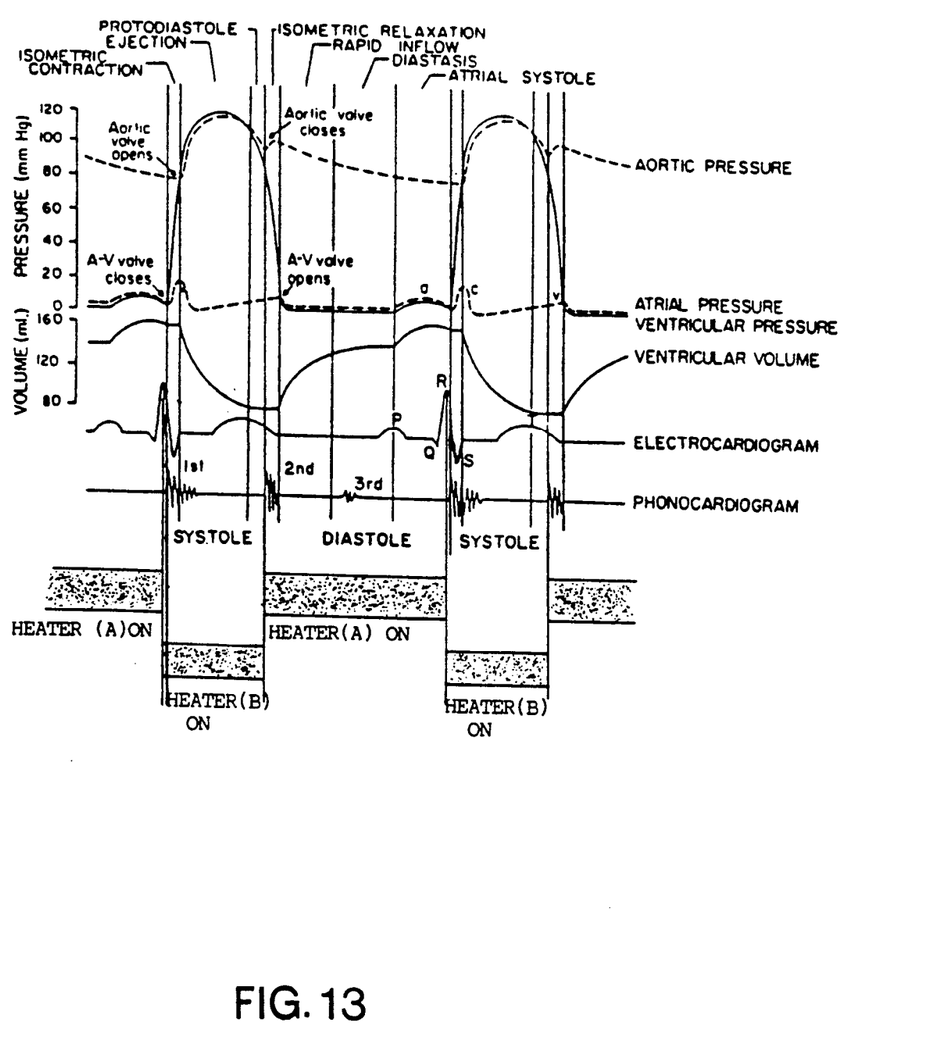
FIG. 13 is a graph of heart pressure and volume over time and shows activation of the electronic switch shown in FIG. 11 by the combined signals of the R wave of an electrocardiogram and the first and second heart sounds.
Figure 14:
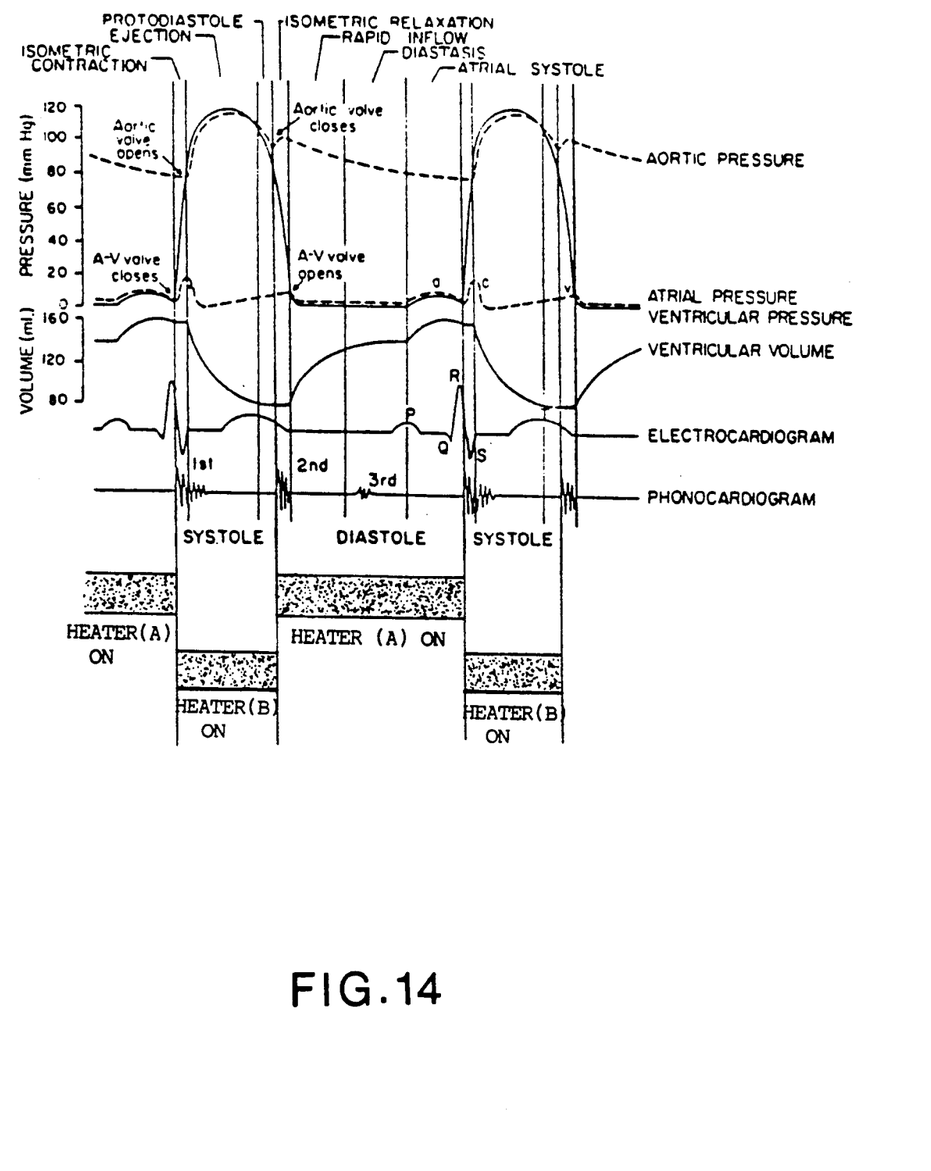
FIG. 14 is a graph of heart pressure and volume over time and shows activation of the electronic switch shown in FIG. 11 by the first and second heart sounds.

As shown in FIGS. 12-14, the length of systolic exposure of the dummy load heater winding B to the high frequency electrical energy is controlled manually according to heart rate and descent of the T wave of the electrocardiogram through a 100 K ohms adjustable potentiometer 64, although this function is preferably carried out through an on-line computer or microprocessor 66.

During diastole blood flow from the left atrium to the left ventricle is mainly laminar during protodiastole and it is characterized by turbulence and reversal of flow during diastases and presystole. Such turbulence and reversal of flow encourage mixing and thermodilution of the thermal indicator introduced. Conversely, systolic blood flow, particularly during the rapid ejection phase, is substantially 100 percent laminar and does not allow mixing or thermodilution of the thermal indicator introduced before reaching the thermometer.

Diversion of the heat pulse wave to the dummy load heater coil B during systole prevents heat dissipation from the heater coil A during systolic laminar flow from the outflow tract of the left ventricle to the thermometer sensor 14 or 33 in the ascending aorta. In addition, this pulsatile type of heating permits the catheter 10 to cool down during systolic intervals.

Temperature in the ascending aorta and the successive temperature increases on applying heat during diastoles in the form of successive square pulse waves is accurately measured by connecting the platinum resistance thermometer 14 or thermistor 33 through interface connections to a thermometer bridge 70 which is in turn connected to a direct current amplifier, recorder 72 and digital computer 66. Total temperature rise of the asymptotic plateau ranges from 0.04–0.06° C.

Two optional electrocardiographic electrodes J and H (FIG. 10) may be mounted on the catheter 10, the first at the distal tip and the second at the proximal point of the catheter 10 designed to be in the aorta. A higher voltage of the R wave devoid of muscle twitches is obtained from the wall of the left ventricle lying between these two electrodes than from skin electrodes.

Calculation of the ejection fraction is carried out by obtaining the mean ratio between three or more successive temperature increases from the middle part of the exponential curve of temperature rise following rhythmic left ventricular ejection. It is calculated either manually or through a microprocessor or computer.

Ejection fraction =

$$r = \frac{\frac{\Delta t_2}{\Delta t_1} + \frac{\Delta t_3}{\Delta t_n} + \frac{\Delta t_4}{\Delta t_3} + \frac{\Delta t_n}{\Delta t_{n-1}}}{n}$$

Where r is the ratio, t is temperature increases and n is the number of values measured.

Calculation of the cardiac output: The left ventricular minute volume (cardiac output) and other volumes as the stroke volume, the residual volume etc. can be calculated from the temperature rise as it approaches the asymptotic plateau $t_P$ and the mean rate of heating $I_r$, $$\text{Cardiac output} = \frac{I_r}{t_p}$$

Where $I_r$ is the mean rate of heating and $t_P$ is the temperature rise as it approaches the asymptotic plateau.

No recirculation problems are expected during the brief 5 seconds required to measure the ejection fraction. However, with lower values of ejection fraction a longer measuring time is required and problems of recirculation may arise.

The asymptotic plateau may be calculated as follows: A large part of the semilogarithmic portion of the curve is first divided into two equal time zones. The temperature rise at the plateau is then calculated from the temperature rise at the midpoint between the two equal times zones $t_m$. The ratio of the temperature rise r, during the second time zone to the temperature rise during the first time zone, $$\frac{\Delta t_s}{\Delta t_f}$$

Where $t_r$ is the first time zone and $t_s$ is the second time zone. This formula may be simplified as follows:

$$\text{Temperature rise} = \frac{\frac{t_m + \Delta t_s}{1 - \Delta t_s}}{\Delta t_f}$$

Where $t_m$ is the midpoint between the two equal time zones. Again, this calculation may be carried out manually or through a microprocessor or computer.

during thermodilution an insignificant rate of heat dissipation occurs through the endocardium to the myocardium. The high velocity of blood flow (mean 1 meter/second) and the short measuring time of 5–10 seconds limit this rate of dissipation to a negligible value. The ease of obtaining multiple measures within a few seconds gives the operator the added advantage of repeating his measures during inspiration and expiration and so consider the mean value as the more accurate ratio of ejection fraction. In addition, the effect of respiration on left ventricular function may be observed.

Successive activations electronic switch in response to the R wave and/or first and second heart sounds as illustrated in FIGS. 12–14.

The electronic switch 42 can be activated by either (a) the R wave of an electrocardiogram or, (b) the combined signals of an electrocardiogram and the first and second heart sounds of a heart amplified by a phonocardiogram or, (c) through the systolic and diastolic changes in intraventricular pressure during the cardiac cycle, obtained through a pressure transducer placed close to the distal tip of the catheter 10.

From the foregoing description it will be understood that the present invention provides a left ventricular cardiac catheter, not only for measuring the left cardiac output but more importantly the specific values of the left ventricular pump function, namely the global left ventricular ejection fraction, but also for providing an accurate diagnostic tool for extensive clinical and research studies on the ejection fraction during diagnostic and interventional catheterization.

I claim:

1. A left ventricular catheter system including a heater winding (A) tightly wound in a bifilar manner on a distal segment of a left ventricular catheter comprising a flexible tubular arrangement with a pigtail distal end adapted to be introduced through a percutaneous introducer with a side port into the femoral artery, and advanced through the aorta and aortic valve until positioned in the cavity of the left ventricle and including a dummy load heater winding (B) of identical impedance to that of the heater winding (A) on said distal segment of said catheter, said heater winding (B) being situated external to the patient receiving said catheter, and said two heater windings (A and B) being connected in such a manner that they can receive alternate pulses of electric energy from a regulated high frequency power supply at a predetermined rate of heating.

2. The left ventricular catheter system of claim 1 wherein said heater winding (A) includes two windings and has two proximal ends and said system further includes wire conductor means for connecting the ends of the heater winding A to three pins on a plug at a proximal end of the catheter.

3. The left ventricular catheter system of claim 2 wherein two pins 1 and 2 of said plug at the proximal end of the catheter are connected to said wire conductor means, to said dummy load heater winding (B) and to a high frequency power supply through said switch means, while pins 2 and 3 of the plug connect heater coil (A) to the high frequency power supply through said switch means, the connections of said wire conductor means serving to direct high frequency energy to the dummy load heater winding (B) during successive systoles via two conductors of the wire conductor means and to heater coil (A) during successive diastoles, whereby a constant environmental temperature is maintained around a measuring thermometer while the pulsatile heat energy is alternately dissipated from heater coil (A) or dummy load heater coil (B).

4. The left ventricular catheter system of claim 1 including switch means which is connected to the windings (A and B) for alternately connecting heater winding (A) or dummy load heater winding (B) to a regulated high frequency power supply and, said switch means being activated by either (a) the R wave of an electrocardiogram or, (b) the combined signals of an electrocardiogram and the first and second heart sounds of a heart amplified by a phonocardiogram or, (c) through the systolic and diastolic changes in intraventricular pressure during the cardiac cycle, obtained through a pressure transducer placed close to the distal top of the catheter.

5. The catheter system of claim 1 wherein said heater winding (A) is at least 4–5 cm long on said distal segment of said catheter, a temperature measuring arrangement is provided at a mean downstream distance of 10 cm from the proximal end of the heater winding (A); and said heater windings (A and B) being connected for alternately receiving electrical energy pulses during systole for winding (B) and during diastole for winding (A) on said distal end of said catheter through switch means.

6. The left ventricular pigtail catheter system of claim 5 wherein electrical energy pulses are diverted to heater winding (B) during successive systoles and received by heater winding (A) during successive diastoles for 5–10 second measuring periods by switch means activated by the R wave of an electro-cardiogram, or the combined signals of the R wave of the electro-cardiogram and the first and second heart sounds amplified through a phonocardiogram, or through the systolic and diastolic pressure values obtained through a pressure transducer placed at a distal point of said catheter.

7. A left ventricular pigtail catheter having a heater winding mounted on a segment of said catheter adjacent a distal end thereof and a platinum resistance thermometer or a thermistor mounted on said catheter at a downstream distance of approximately 10 cm from a proximal end of said heater winding (A), a dummy load heater winding (B) situated external of a patient and adapted to receive electrical energy pulses diverted from heater winding (A) during successive systoles of 5–10 second measuring period, said electrical energy pulses being triggered through switch means by the R wave of an electrocardiogram or the combined signals of the R wave and the first and second heart sounds amplified through a phonocardiogram, or through the changing pressure values during the cardiac cycles obtained through a pressure transducer close to the tip of the catheter whereby multiple measures of the ejection fraction of the left ventricle and for the minute volume in clinical studies of the left ventricle pump function can be taken during a diagnostic evaluation, an interventional catheterization, or in intensive care, before and after cardiac surgery and whenever determination of the ejection fraction of the left ventricle is desired.

* * * * *